United States Patent
Gu

(10) Patent No.: US 9,102,914 B2
(45) Date of Patent: Aug. 11, 2015

(54) 3D TROPHOBLAST MATRIX FOR PREPARING ORGAN-SPECIFIC STEM CELLS

(75) Inventor: Yansong Gu, Bellevue, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 0 days.

(21) Appl. No.: 13/257,949

(22) PCT Filed: Feb. 3, 2011

(86) PCT No.: PCT/US2011/023591
§ 371 (c)(1),
(2), (4) Date: Sep. 20, 2011

(87) PCT Pub. No.: WO2012/105979
PCT Pub. Date: Aug. 9, 2012

(65) Prior Publication Data
US 2012/0202261 A1    Aug. 9, 2012

(51) Int. Cl.
| | | |
|---|---|---|
| C12N 15/85 | (2006.01) | |
| A61K 35/00 | (2006.01) | |
| C12N 5/07 | (2010.01) | |
| C12N 5/0735 | (2010.01) | |
| C12N 11/04 | (2006.01) | |
| C12N 11/08 | (2006.01) | |
| C12N 11/10 | (2006.01) | |
| C12N 5/077 | (2010.01) | |

(52) U.S. Cl.
CPC ............. *C12N 5/06* (2013.01); *C12N 5/0606* (2013.01); *C12N 11/04* (2013.01); *C12N 11/08* (2013.01); *C12N 11/10* (2013.01); *C12N 5/0657* (2013.01); *C12N 2501/00* (2013.01); *C12N 2502/025* (2013.01); *C12N 2506/02* (2013.01); *C12N 2533/30* (2013.01); *C12N 2533/90* (2013.01)

(58) Field of Classification Search
CPC ........ C12N 11/04; C12N 11/08; C12N 11/10; C12N 2502/025; C12N 2533/30; C12N 5/0606
See application file for complete search history.

(56) References Cited

U.S. PATENT DOCUMENTS

| | | | |
|---|---|---|---|
| 5,567,435 A | 10/1996 | Hubbell et al. | |
| 5,567,440 A | 10/1996 | Hubbell et al. | |
| 5,627,233 A | 5/1997 | Hubbell et al. | |
| 5,628,863 A | 5/1997 | Lee | |
| 5,654,381 A | 8/1997 | Hrkach et al. | |
| 5,843,780 A | 12/1998 | Thomson | |
| 6,365,149 B2 | 4/2002 | Vyakarnam et al. | |
| 6,471,993 B1 | 10/2002 | Shastri et al. | |
| 2009/0203129 A1 | 8/2009 | Furcht et al. | |
| 2009/0239298 A1 | 9/2009 | Gerecht et al. | |

FOREIGN PATENT DOCUMENTS

WO    WO 2004/050826    6/2004

OTHER PUBLICATIONS

Ma et al., Sep. 20, 2011, A33.*
Vidarsson et al (Stem Cell Rev and Rep, 6: 108-120, 2010).*
Bauwens et al (Biotechnology and Bioengineering, 90(4): 452-461, 2005).*
Adelman et al., The BMP/BMPR/Smad pathway directs expression of the erthroid-specific EKLF and GATA1 transcription factors during embryoid body differentiation in serum-free media, Development, (2002), 129(2):539-549.
Amit et al, Derivation and spontaneous differentiation of human embryonic stem cells, Journal of Anatomy, (2002), 200:225-232.
Bongso et al., Improved quality of human embryos when co-cultured with human ampullary cells, Hum Reprod., (1989), 4(6):706-713.
Bottcher et al., Fibroblast growth factor signaling during early vertebrate development, Endocr Rev., (2005), 26(1):63-77.
Bratt-Leal et al., Engineering the embryoid body microenvironment to direct embryonic stem cell differentiation, Biotechnol Prog., (2009), 25(1):43-51.
Campagnolo et al., EGFL7 is a chemoattractant for endothelial cells and is up-regulated in angiogenesis and arterial injury, Am J Pathol., (2005), 167(1):275-284.
Chinzei et al., Embryoid-body cells derived from a mouse embryonic stem cell line show differentiation into functional hepatocytes, Hepatology, (2002), 36(1):22-29.
Dang et al., Efficiency of embryoid body formation and hematopoietic development from embryonic stem cells in different culture systems, Biotechnol Bioeng., (2002), 78(4):442-453.
Dawson et al, Biomaterials for stem cell differentiation, Advanced Drug Delivery Reviews, (2008), 60:215-228.
Gardner et al., Culture and transfer of human blastocysts increases implantation rates and reduces the need for multiple embryo transfers, Fertil Steril., (1998), 69(1):84-88.
Gerecht et al, Hyaluronic acid hydrogel for controlled self-renewal and differentiation of human embryonic stem cells, Proceedings of the National Academy of Sciences of the USA, (2007), 104(27):11298-11303.
Gerecht-Nir et al., Bioreactor cultivation enhances the efficiency of human embryoid body (hEB) formation and differentiation, Biotechnol Bioeng, (2004), 86(5):493-502.
Hutmacher, Scaffold design and fabrication technologies for engineering tissues—state of the art and future perspectives, J Biomater Sci Polym Ed., (2001), 12(1):107-124.
Hwang et al., Microwell-mediated control of embryoid body size regulates embryonic stem cell fate via differential expression of WNT5a and WNT11, Proc Natl Acad Sci USA, (2009), 106(40):16978-16983.
International Search Report and Written Opinion dated Apr. 15, 2011 in application PCT/US2011/0235591.

(Continued)

*Primary Examiner* — Peter Paras, Jr.
*Assistant Examiner* — Magdalene Sgagias
(74) *Attorney, Agent, or Firm* — Foley & Lardner LLP

(57) ABSTRACT

This disclosure relates generally to methods, apparatuses, and cellular compositions and cellular products that use a unique trophoblast-containing 3D matrix as a compartmental chamber for growing embryoid bodies that can be induced to differentiate into organ-specific cell types.

16 Claims, 1 Drawing Sheet

(56) References Cited

OTHER PUBLICATIONS

Jurvansuu et al., Transmembrane protein 18 enhances the tropism of neural stem cells for glioma cells, Cancer Res., (2008), 68(12):4614-4622.
Khetan et al., Cellular encapsulation in 3D hydrogels for tissue engineering, J Vis Exp., (2009), 32:1590-1594.
Kurosawa et al, Methods for inducing embryoid body formation: in vitro differentiation system of embryonic stem cells, J Biosci Bioeng, (2007), 103(5):389-398.
Levenberg et al, Differentiation of human embryonic stem cells on three-dimensional polymer scaffolds, Proceedings of the National Academy of Sciences of the USA, (2003), 100(22):12741-12746.
Ma et al., Effects of pore size in 3-D fibrous matrix on human trophoblast tissue development, Biotechnol Bioeng., (2000), 70(6):606-618.
Ma et al, Oxygen tension influences proliferation and differentiation in a tissue-engineered model of placental trophoblast-like cells, Tissue Eng, (2001), 7(5):495-506.
Ma, et al, Tissue Engineering Human Placenta Trophoblast Cells in 3-D Fibrous Matrix: Spatial Effects on Cell Proliferation and Function, Biotechnology Progress, (1999), 15:715-724.
Ma et al., Impaired B-lymphopoiesis, myelopoiesis, and derailed cerebellar neuron migration in CXCR4- and SDF-1-deficient mice, Proc Natl Acad Sci USA, (1998), 95(16):9448-9453.
Ma et al., The chemokine receptor CXCR4 is required for the retention of B lineage and granulocytic precursors within the bone marrow microenvironment, Immunity, (1999), 10(4):463-471.
McGrath et al., Embryonic expression and function of the chemokine SDF-1 and its receptor, CXCR4, Dev Biol., (1999), 213(2):442-456.
Omi et al, Establishment of an immortalized human extravillous trophoblast cell line by retroviral infection of E6/E7/hTERT and its transcriptional profile during hypoxia and reoxygenation, Int J Mol Med, (2009), 23(2):229-36.
Primo et al., Essential role of PDK1 in regulating endothelial cell migration, J Cell Biol., (2007), 176(7):1035-1047.
Quackenbush et al., Eotaxin modulates myelopoiesis and mast cell development from embryonic hematopoietic progenitors, Blood, (1998), 92(6):1887-1897.
Soto-Gutierrez et al., Attachment evaluation of embryonic stem cells on a PAU-coated non-woven fabric: A potential source for bioartificial assist devices, E-Gnosis(online), (2006) 4(10):1-10.
Thomson et al, Isolation of a primate embryonic stem cell line, Proc Natl Acad Sci USA, (1995), 92(17):7844-7848.
Thomson et al., Embryonic stem cell lines derived from human blastocysts, Science, (1998), 282(5391):1145-1147.
Thomson et al., Primate embryonic stem cell, Curr Top Dev Biol., (1998), 38:133-165.
Tian et al., Cytokine requirements differ for stroma and embryoid body-mediated hematopoiesis from human embryonic stem cells, Exp Hematol., (2004), 32(10):1000-1009.
Levenberg, Shulamit et al., "Endothelial cells derived from human embryonic stem cells," Proceedings of the National Academy of Sciences of the USA, (Apr. 2, 2002), vol. 99, No. 7, pp. 4391-4396.
Handy, S.T., "Room Temperature Ionic Liquids: Different Classes and Physical Properties," Current Organic Chemistry, vol. 9, No. 10, pp. 959-988 (Jul. 2005).
Keung, A.J., "Biophysics and dynamics of natural and engineered stem cell microenvironments," Advanced Review, vol. 2, pp. 49-64 (2009).
Li, Z., et al., "Functional and Transcriptional Characterization of Human Embryonic Stem Cell-Derived Endothelial Cells for Treatment of Myocardial Infarction," vol. 4, No. 12, e8443 (13 pages), (Dec. 2009).
Zhang et al., "Physical Properties of Ionic Liquids: Database and Evaluation," Journal of Physical and Chemical Reference Data, vol. 35, No. 4, pp. 1475-1517 (Oct. 10, 2006).

\* cited by examiner

A. Seeding hESCs into 3D trophoblast matric
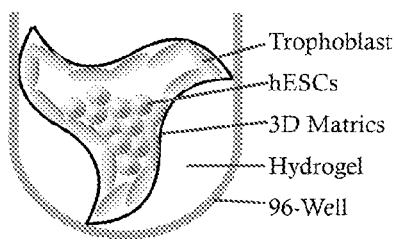
B. Growing embryoid body
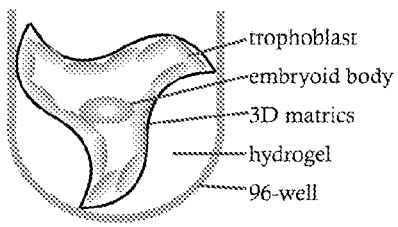
C. Loosening up embryoid body
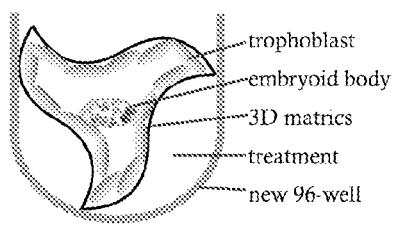
D. Isolating OSCs
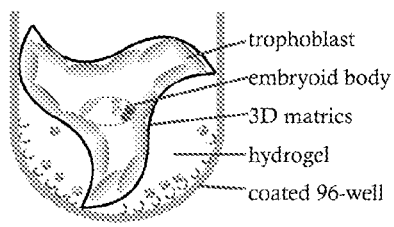

3D TROPHOBLAST MATRIX FOR PREPARING ORGAN-SPECIFIC STEM CELLS

CROSS REFERENCE TO RELATED APPLICATIONS

This application is the U.S. national stage application under 35 U.S.C. 0371 of International Patent Application No. PCT/US2011/023591, filed on Feb. 3, 2011, which is incorporated herein by reference in its entirety.

TECHNICAL FIELD

This disclosure relates generally to methods, apparatuses, and compositions for producing and isolating organ-specific stem cells from a trophoblast-encased matrix.

BACKGROUND

The following description is provided to assist the understanding of the reader. None of the information provided or references cited is admitted to be prior art.

Organ-specific stem cells (OSCs) are specialized stem cells that have committed to differentiating into specific lineages of somatic cells. Unlike human embryonic stem cells (hESCs), there is little, if any, risk that organ-specific stem cells create tumors after they are transplanted into the body. Organ-specific stem cells are the ideal source of stem cells for clinical applications of tissue repairing and regenerative medicine. More recently, hESCs, including induced pluripotent stem cells (iPSCs), have become readily available for exploring their clinical applications. Although hESCs are capable of differentiating into all lineages of somatic cells, it is difficult to control hESC differentiation and the risk of tumor formation. Thus, the main problem that limits the current development of stem cell therapy is how to obtain OSCs from hESCs.

SUMMARY

One aspect of the present technology is a method for creating and isolating organ-specific stem cells, comprising seeding embryonic stem cells into a trophoblast-containing three-dimensional matrix; growing an embryoid body from the embryonic stem cells within the trophoblast-containing matrix; and transferring the matrix containing the embryoid body to a new environment that contains at least one agent selected to induce differentiation of and/or chemoattract organ-specific stem cells; wherein the organ-specific stem cells migrate out of the embryoid body and the matrix. In one embodiment, the method further comprises encapsulating embryonic stem cells in a hydrogel. In one embodiment, the embryonic stem cells are seeded into an agarose microbead. In one embodiment, the hydrogel comprises a natural or synthetic polymer. In another embodiment, the hydrogel comprises a polysaccharide, a peptide, a proteoglycan, or a combination thereof. In another embodiment, the hydrogel comprises a polymer selected from the group consisting of poly(glycolic acid), poly(lactic acid), poly(glycolic acid-co-lactic acid), aollagen, laminin, hyaluronan, alginate, chitosan, silk fibrils, poly(vinyl alcohol), poly(2-hydroxylethyl methacrylate), polyethylene terephthalate, agarose, methylcellulose, fibrin, and a combination thereof. In one embodiment, the trophoblast-containing matrix is embedded in a hydrogel that is in a well of a 96-well plate. A three dimensional matrix that has a surface to which is adhered or affixed one or more trophoblast cells is a trophoblast-containing matrix of the present technology.

In one embodiment, the method further comprises degenerating the structure of the embryoid body once it has formed from the differentiating embryonic stem cells. In one embodiment the embryoid body is degenerated using trypsin. In a further embodiment, degenerating the structure of the embryoid body comprises dissolving the hydrogel and digesting an extracellular matrix associated with the embryoid body. In another embodiment, the method further comprises isolating organ-specific stem cells from the hydrogel.

In another embodiment, the step of transferring the matrix containing the embryoid body to a new environment comprises (i) dissolving the hydrogel and (ii) transferring the trophoblast-containing matrix into a different well in the 96-well plate that is either (a) pre-filled with a hydrogel that comprises at least one agent for promoting the creation of organ-specific stem cells, or (b) coated with at least one agent for promoting the creation of organ-specific stem cells. In one embodiment, the agent is a chemokine or morphogen.

In another embodiment, the trophoblasts that are contained in and on the matrix are cytotrophoblast cells. In another embodiment, the embryonic stem cells are human embryonic stem cells. In another embodiment, 1-100,000 embryonic stem cells are seeded into the trophoblast-containing matrix. In another embodiment, the agent(s) promotes the creation of organ-specific stem cells corresponding to those derived from the ectoderm, endoderm, and/or mesoderm, including but not limited to, neural stem cells, oligodendrocyte cells, myelinate cells, mast cells, hemato-lymphoid cells, epithelial cells, mammary stem cells, mesenchymal stem cells, olfactory stem cells, and testicular stem cells.

In another embodiment, multiple wells of a 96-well plate each contain a trophoblast-containing matrix seeded with embryonic stem cells, and each matrix, when it comprises a suitably grown embryoid body, is simultaneously or subsequently transferred to a new well that comprises at least one agent that promotes creation of the same or different organ-specific stem cell. In one embodiment, the matrix is transferred to a new environment once the embryoid body develops beating cardiomyocytes.

Another aspect of the present technology is a trophoblast-containing, three dimensional matrix, comprising a permeable enclosure with an opening, wherein trophoblast cells are adhered to the material used to form the matrix. In one embodiment, the trophoblasts are cytotrophoblast cells. In another embodiment, the trophoblast-containing, three dimensional matrix further comprises at least one embryonic stem cell in the enclosure. In another embodiment, the trophoblast-containing, three dimensional matrix further comprises an embryoid body in the enclosure.

In one aspect, the present technology provides a method for creating and isolating organ-specific stem cells, comprising (1) seeding embryonic stem cells into a three-dimensional matrix that comprises trophoblast cells, (2) growing an embryoid body from the embryonic stem cells within the trophoblast-containing matrix; (3) transferring the matrix containing the embryoid body to an environment that comprises at least one agent that promotes cellular differentiation and/or cellular migration of organ-specific stem cells from the embryoid body. In one embodiment, the matrix is embedded within a hydrogel. In another embodiment, the agent is a morphogen. In another embodiment, the agent is a chemoattractant. In another embodiment, the organ-specific stem cells migrate out of the embryoid body and away from the matrix. In another embodiment, the trophoblasts are cytotrophoblast cells.

Thus, in one aspect, a method for obtaining organ-specific stem cells comprises seeding embryonic stem cells into a three-dimensional matrix that comprises trophoblast cells, growing an embryoid body from the embryonic stem cells within the matrix; and transferring the matrix containing the embryoid body to an environment that induces organ-specific stem cells to migrate out of the embryoid body and out of the matrix.

In one embodiment, the three dimensional matrix is made from a natural or synthetic biomaterial. In one embodiment, the biomaterial is a synthetic biomaterial selected from the group consisting of polyethylene terephthalate (PET), poly-amino-urethan-coated unwoven polytetrafluoroethylene (PTFE), poly-1-lactic acid (PLLA), polyglycolic acid (PGA), polylactide-co-glycolide (PLGA), poly(ε-caprolactone) (PCL) and combinations thereof. In another embodiment, the matrix is a natural biomaterial selected from the group consisting of collagen, fibrinogen, fibrin, hyaluronic acid, alginate, coralline, glycosaminoglycans (GAGs), hydroxyapatite (HA), cellulose, chitosan, silk fibroin and Matrigel.

In another embodiment the three dimensional matrix is exposed to a serum-free environment comprising an agent selected from the group consisting of growth factors, stem cell factor (SCF), thrombopoietin (TPO), Flt-3 ligand (Flt-3L), bone morphogenic protein-4 (BMP-4), vascular endothelial growth factor (VEGF), and combinations thereof.

In another embodiment, the hydrogel may include a natural or synthetic polymer, a polysaccharide, a peptide, or a proteoglycan. Examples of the hydrogel include, without limitation, poly(glycolic acid), poly(lactic acid), poly(glycolic acid-co-lactic acid), collagen, laminin, hyaluronan, alginate, chitosan, silk fibrils, poly(vinyl alcohol), poly(2-hydroxyl ethyl methacrylate), polyethylene terephthalate, agarose, methylcellulose, and fibrin. In another embodiment, the hydrogel in which the three-dimensional matrix is embedded comprises an agent, selected from the group consisting of retinoic acid, transforming growth factor β, activin-A, insulin-like growth factor, bone morphogenic protein-4 (BMP-4), acidic fibroblast growth factor, bFGF, vascular endothelial growth factor (VEGF), SCF, erythropoietin, thyroid hormone, and eotaxin, and combinations thereof.

In one embodiment, the matrix is embedded in a hydrogel that is in a well of a 96-well plate. In another embodiment, the step of transferring the matrix containing the embryoid body to a new environment comprises dissolving the hydrogel and transferring the trophoblast-containing matrix into a different well in the 96-well plate that is either pre-filled with a hydrogel that comprises at least one agent for promoting the creation of organ-specific stem cells, or coated with at least one agent for promoting the creation of organ-specific stem cells. In another embodiment, multiple wells of the 96-well plate each contain a trophoblast-containing matrix seeded with embryonic stem cells, and each matrix, when it comprises a suitably grown embryoid body, is simultaneously or subsequently transferred to a new well that comprises at least one agent that promotes creation of the same or different organ-specific stem cell.

In another embodiment, the environment to which the three-dimensional matrix is transferred comprises a chemoattractant, selected from the group consisting of stromal cell-derived factor-1 (SDF-1) chemokine, chemokine monocyte chemoattractant protein-1, cytokine stem cell factor, EGFL7 protein, serine/threonine protein kinase phosphoinositide-dependent kinase 1 (PDK1) and FGF. In another embodiment, the environment to which the three-dimensional matrix is transferred comprises a chemoattractant that facilitates glioma tracking, selected from the group consisting of stromal cell-derived factor-1 (SDF-1) chemokine, chemokine monocyte chemoattractant protein-1 and cytokine stem cell factor.

In one embodiment, the agent is a chemokine or morphogen. In one embodiment, the agent(s) promotes the creation of neural stem cells, oligodendrocyte cells, myelinate cells, mast cells, hemato-lymphoid cells, epithelial cells, mammary stem cells, mesenchymal stem cells, olfactory stem cells, and testicular stem cells.

In one embodiment, the embryonic stem cells are human embryonic stem cells. In another embodiment, 1-100,000 embryonic stem cells are seeded into the trophoblast-containing matrix. In another embodiment 1-100, 100-200, 200-300, 300-400, 400-500, 500-600, 600-700, 700-800, 800-900, 900-1,000, 1,000-2,000, 2,000-3,000, 3,000-4,000, 4,000-5,000, 5,000-6,000, 6,000-7,000, 7,000-8,000, 8,000-9,000, 9,000-10,000, 10,000-50,000, 50,000-100,000, or more than 100,000 ES cells are seeded into the trophoblast-containing matrix.

In another embodiment, the matrix is transferred to a new environment once the embryoid body develops. An indicator of suitable embryoid body development are beating cardiomyocytes.

Another aspect of the present technology is a trophoblast-containing, three dimensional matrix, comprising a permeable enclosure with an opening, wherein the enclosure comprises trophoblast cells that secrete nutrients into the enclosure. In one embodiment, the trophoblasts are cytotrophoblast cells. In one embodiment, therefore, such technological components for practicing the methods described herein are in a kit. In one embodiment, the kit comprises at least one or more of a pre-made or pre-configured three-dimensional matrix, a fabric that can be configured into a three-dimensional matrix, a tube, vial, or vessel comprising trophoblast cells, and one or more vials comprising activation or differentiation agents such as those disclosed elsewhere herein.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE FIGURES

FIG. 1(A-D). Schematic overview of four steps involved in producing and isolating organ-specific cells: A. Seeding ES cells, B. Growing EBs, C. Treating EBs, and D. Isolating Cells.

DETAILED DESCRIPTION

In the following detailed description, reference may be made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented here.

As used herein, unless otherwise stated, the singular forms "a," "an," and "the" include plural reference. Thus, for example, a reference to "a protein" includes a plurality of proteins.

As used herein, the term "about" will be understood by persons of ordinary skill in the art and will vary to some extent depending upon the context in which it is used. If there are uses of the term which are not clear to persons of ordinary skill in the art, given the context in which it is used, the term "about" in reference to quantitative values will mean up to plus or minus 10% of the enumerated value.

1. Embryonic Stem Cells

Embryonic stem (ES) cells are capable of differentiating into all somatic cell lineages. Undifferentiated stem cells are pluripotent cells that retain self renewal capability and the developmental potential to differentiate into a wide range of cell lineages including the germ line. In contrast, cells present in formed EBs, as discussed below, are considered multipotent since they have partially differentiated to form the three germ layers characteristic of EBs. ESCs of the present technology can be obtained from the embryonic tissue formed after gestation or embryonic germ cells. Stem cell derivation and preparation is further described hereinbelow. ES cells, for instance, can be obtained using well-known cell-culturing methods, such as but not limited to those disclosed in US 20090239298 and the references cited therein. For example, human ESCs can be isolated from human blastocysts obtained from human in vivo pre-implantation embryos or from in vitro fertilized (IVF) embryos. Alternatively, a single cell human embryo can be expanded to the blastocyst stage. They also can be derived from human embryonic germ cells (EGCs) prepared from the primordial germ cells using laboratory techniques well known to the skilled artisan. See, for example, US 20090239298. ES cells, such as BG01, BG02, BG03, BG04, CY12, CY30, CY92, CY10, TE03 and TE32, also are available commercially for purchase from, for instance, the NIH human embryonic stem cells registry (escr.nih.gov). Li et al., PloS ONE, 4(12), e8443, pp.: 1-13 (December 2009), which is incorporated herein by reference, describe a two-step in vitro differentiation method for obtaining endothelial cell differentiation that involves growing undifferentiated hESCs on Matrigel-coated plates and subsequently culturing them in differentiation medium containing Iscove's modified Dulbecco's medium, and 15% Knockout® Serum Replacement, various amino acids, and VEGF. See page 2 under Materials and Methods. This culturing induces the formation of suspended embryoid bodies, which were induced to sprout in collagen type I followed by further incubation and addition of EGM-2 medium. Id. See also the following for details on methods of preparation human ESCs: U.S. Pat. No. 5,843,780; Science 282: 1145, 1998; Curr. Top. Dev. Biol. 38: 133, 1998; Proc. Natl. Acad. Sci. USA 92: 7844, 1995; Bongso et al., Hum Reprod 4: 706, 1989; and Gardner et al., Fertil. Steril. 69: 84, 1998; all of which are incorporated herein by reference.

2. Embedding ES Cells in Hydrogels

ES cells are routinely cultured on mouse embryonic fibroblast feeder layers or on surfaces coated with Matrigel, laminin, fibronectin, and human serum in MEF-conditioned medium. See Gerecht et al., PNAS, 104(27), pp. 11298-11303 (2007), which is incorporated herein by reference. Gerecht explored the encapsulation of human ES cells in hydrogel scaffolds in order to produce a 3D culture system for maintaining ES cells in an undifferentiated state prior to being induced to differentiate in response to specific cues. Gerecht concluded that hyaluronic acid-based hydrogels can maintain the undifferentiated state of human ES cells in the presence of conditioned medium from MEFs until soluble factors (described below) are introduce to direct cell differentiation. See Gerecht for specific encapsulation methods. See also Khetan and Burdick, Journal of Visualize Experiments, 32, pp.: 1-4 (2009), which is incorporated herein by reference for detailed methods for encapsulating cells in hydrogels.

Hyaluronic acid (HA) can be added to ES cell culture, or used to modify matrix or scaffold or other such biomaterial surfaces to maintain ES cells in an undifferentiated state. And as discussed above it is also possible to encapsulate ES cells in hydrogels comprising, or made of, hyaluronic acid. For instance, HA can be modified with photoreactive groups and colonies of human ES cells suspended in a solution of the modified HA and the photoinitiator PBS. One favorable hydrogel for this purpose is one containing 2 wt % of a 50-kDa macromer that maintains the viability of differentiated mammalian cells. See Gerecht et al., page 11299. The hydrogel of HA can then be photopolymerized into a hydrogel network by exposing the cells and solution to UV light.

Gerecht, for instance, describes the use of methacrylated hyaluronic acid dissolved at a concentration of 2 wt % in PBS containing 0.05 wt % 2-methyl-1-[4-(hydroxyethoxy)phenyl]-2-methyl-1-propanone (Irgacure 2959), to which hESCs were added at $0.5$-$1 \times 10^7$ cells per milliliter of precursor solution. The mixture was pipetted into a sterile mold at 50-μl per well to obtain discs with diameters of 3 mm and thicknesses of 2 mm, and then photopolymerized. For differentiation, gels were cultured with endothelial growth medium (Cambrex) supplemented with 100 ng/ml VEGF (R & D Systems). Gerecht also explained that to release encapsulated hESCs, HA hydrogels were incubated for 24 h in hESC growth medium containing 100, 500, 1,000, or 2,000 units/ml hyaluronidase (Sigma). The percentage of viable hESCs incubated with 2,000 units/ml HAase for 24 h or 1 mg/ml collagenase IV for 30 min was examined by trypan blue. Cells were then collected, centrifuged, washed three times with PBS to remove any hydrogel residues, resuspended in growth medium, and cultured on MEF-coated dishes according to standard methods.

Gerecht also reported that high cell concentrations in the range of $5$-$10 \times 10^6$ cells per milliliter of solution were essential for high viability and sustained cell growth (page 11300). At concentrations greater than $10 \times 10^6$ cells per milliliter, large clumps of cells formed that induced rapid apoptosis whilst concentrations lower than $5 \times 10^6$ cells per milliliter may not adequately support colony formation. Gerecht's ES-encapsulated HA hydrogel was cultured on MEF conditioned medium for a week and then replaced by angiogenic differentiation medium containing VEGF. Cell sprouting and elongation was observed and after 1 week of differentiation staining with specific vascular markers showed that most cells had differentiated into smooth muscle actin. Gerecht at page 11302. See Gerecht's Materials and Methods beginning at page 11302 for specific media compositions and method steps.

It can be desirable to seed stem cells in a manner that enables even distribution of the cells within the three-dimensional matrix. One method to achieve even distribution is seeding under a centrifugal force. See Materials and Experimental Procedures in US 20090239298. Basically, cells are seeded at a concentration that ensures entrapment within the matrix and maximal formation of EBs. According to the present technology hESCs are seeded at $5 \times 10^6$ cells per $cm^3$ matrix, $2.5 \times 10^7$ cells per $cm^3$ matrix, or $5 \times 10^7$ cells per $cm^3$ matrix.

3. Embryoid Bodies

ES cells aggregate together to form an embryoid body (EB); it is the cells of the EB that differentiate into specific lineages of cells. For instance, hematopoietic cells can differentiate into erythoid cells, neutrophils, megakaryocytes, and lymphoid cells; neural stem cells can differentiate into neurons and glial cells; and mesenchymal stem cells differentiate into muscle, bone, cartilage, fat, marrow stroma, and tendons, and also into the visceral mesoderm, which subsequently differentiates into cardiac muscle, smooth muscle, and endothelial and hemapoietic progenitor cells. Endothelial cells in turn can form blood vessels and are helpful for regenerating myocardial cells, and inducing angiogenesis.

The embryoid body forms all three germ layers: the embryonic endoderm, the embryonic mesoderm, and the embryonic ectoderm. Cells of the embryonic endoderm differentiate into, for instance, hepatocytes and pancreatic cells. Cells of the embryonic mesoderm differentiate into specific lineages such as, but not limited to, osseous cells, cartilageous cells, elastic tissue, fibrous connective tissue, myoctes, myocardial cells, bone marrow cells, vascular cells (both endothelial and smooth muscle), and hematopoietic cells. Cells of the embryonic ectoderm differentiate into, for instance, neural cells, retinal cells, and epidermal cells. The present technology also is useful for producing cell lines by immortalizing the EB-derived cells by methods known in the art, including, for example, expressing a telomerase gene in the cells or co-culturing the cells with NIH 3T3 hph-HOX11 retroviral producer cells.

4. Formation of Embryoid Bodies

There are well-known methods for inducing the formation of embryoid bodies (EBs) from embryonic stem (ES) cells. For instance, EBs can be formed using liquid suspension methods, incubation in methylcellulose semisolid medium, the hanging drop method, and in 96-well plates and conical tubes. Methylcellulose culture is useful for EB formation from a clonal origin and generally is used for hematopoietic differentiation. See Kurosawa, J Biosci Bioeng. 103: 389-398. (2007), and Hwang et al., PNAS, 106(4), pp. 16978-16984 (2009), which are incorporated herein by reference.

As is also well known, ES cells can differentiate into various cell lineages and cell types by first forming EBs. Variations in the size of the embryoid body can lead to differentiation of different types of cells. Thus, heterogeneity in EB formation can lead to formation of a variety of different cell types. The hanging drop culture method produces EBs of controlled size in liquid drops of typically less than 50 μl. EB size is important because the size of the embryoid body is another factor that determines the kind of cells and lineages that will differentiate from the embryoid body. Hwang et al. (2009) showed that uniformly formed EBs within microwells differentiated when certain self-renewing factors were removed by the loss of expression of Oct4, E-cadherin, and SSEA-1. See page 16981. In vitro EB formation results in primordial precursor cells that further differentiate into specialized phenotypes of cardiac and vascular tissue. Large EBs supported cardiac differentiation, while smaller EBs generated endothelial cells. Furthermore, hESCs can be placed within a hydrogel microbead, such as those made of agarose, prior to placing them in the matrix.

5. Numbers of ES Cells and EB Sizes

Thus, depending on how many ES cells are seeded together to form cellular aggregates, the size of the eventual embryoid body will vary. Accordingly, for instance, an EB of about 450 μm typically induces cardiogenesis and the expression of Wnt11, while a smaller EB of about 150 μm induces endothelial cell formation with the expression of Wnt5a. See Hwang et al., PNAS, vol. 106, no. 40: 16978-16983 (2009). Accordingly, the present technology encompasses the growth of EBs from hESCs into EB sizes where at least 80% or at least 90% of the EBs described herein have a size of about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, about 210 μm, about 220 μm, about 230 μm, about 240 μm, about 250 μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, about 400 μm, about 410 μm, about 420 μm, about 430 μm, about 440 μm, about 450 μm, about 460 μm, about 470 μm, about 480 μm, about 490 μm, or about 500 μm, or more than about 500 μm. Thus, sizes of EBs encompassed by the present technology from which organ-specific stem cells can be differentiated include but are not limited to EBs that are 10-100 μm in size, 100-200 μm in size, 200-300 μm in size, 300-400 μm in size, 400-500 μm in size, 500-600 μm in size, or greater than 600 μm in size.

6. General Methods for Forming EBs

A suspension culture method of forming EBs is the most basic method where EBs form from small clumps of ES cells. This produces EBs of low homogeneity in morphology and differentiation. Round-bottomed 96-well plates also are useful for making EBs with controlled size. The present technology is not limited to the use only of 96-well plates. Other vessels for holding and manipulating the matrices described herein for growing and differentiating embryoid bodies can be used. For instance, large numbers of EBs can be produced using flasks and bioreactors and stirred-suspension cultures, or different type of plates containing wells—not only the 96-well type format—can be used, such as 96-well, high-volume plate has a capacity of 4 mL per well, and also 48-well plates are available in three versions, offering 5, 7 and 10 mL per well, respectively; one may also use a 24-well plate offering 10 mL per well and the standard 45-mm height of a deep well plate; or any size well and volume of chamber can be used according to the present invention. Thus, there are several methods for inducing the formation of EBs from ES cells. Kurosawa, Journal of Bioscience and Bioengineering, Volume 103, Issue 5, May 2007, pages 389-398, describes three basic methods: liquid suspension culture in bacterial-grade dishes, culture in methylcellulose semisolid media, and culture in hanging drops. Also described are methods using a round-bottomed 96-well plate and a conical tube adopted for forming EBs from predetermined numbers of ES cells. For the production of large numbers of EBs, stirred-suspension culture using spinner flasks and bioreactors is performed. Large-scale formation of human EBs in a dynamic culture using a rotating cell culture system is described in PCT Pat. Appl. No. IL 03/01017 and Gerecht-Nir (2004) Biotechnol. Bioeng. 86: 493-502, which are incorporated herein by reference.

Accordingly, there exist numerous approaches for generating stem cell-derived-differentiated cells for forming embryoid bodies. US 20090239298, which is incorporated herein by reference, describes how EBs are formed following the removal of ESCs from feeder layer or matrix-based cultures into suspension cultures, and that the formation of ESC aggregates is an important step in producing EBs. The extent of aggregation should be carefully monitored and controlled since large agglomerated EBs are often characterized by extensive cell death and necrosis due to mass transport limitations. See Dang et al. (2002). Biotechnol. Bioeng. 78:442-453, which is incorporated herein by reference.

7. Matrices Comprising Trophoblast Cells

The present technology produces EBs inside a unique matrix that comprises trophoblast cells. Trophoblasts are cells that form the outer layer of a blastocyst, and ultimately become the fetal compartment of the placenta during pregnancy. Human trophoblasts differentiate to become villous or extravillous. Multinucleate syncytiotrophoblasts form the epithelial layer of the villi and are responsible for exchanging gas and providing nutrients between the mother and the fetus. Mononuclear extravillous cytotrophoblasts are invasive cells. Cytotrophoblast cells also can differentiate, migrate and invade into the uterine stroma in early pregnancy, and can fuse to form other syncytiotrophoblasts or aggregate to form an anchoring-type of villous trophoblasts. A sub-category, the extravillous trophoblasts, are the invasive kind, which invade into the uterine wall and its blood vessels, particularly the spiral arteries. Oxygen tension, levels, and exposure is an important factor in cellular differentiation of trophoblast cells. See Ma et al., Tissue Eng. 7(5):495-506 (2001). There are three forms of cytotrophoblast differentiation: (1) the villous syncytiotrophoblasts which make placenta hormones, such as hCG and hPL; (2) extravillous anchoring trophoblasts, which produce fibronectin-trophouteronectin for attaching the placenta to the uterus; and (3) invasic intermediate trophoblasts, which produce lactogen, u-PA, and PAL-1. Trophoblast cells (which are also known in the art as $ED_{27}$ cells) can be obtained from human first-trimester chorionic villi. See Ma et al., Biotechnol. Prog., 15:715-724 (1999). See also Bratt-Leal et al., Biotechnol Prog. 25(1):43-51 (2009). It also is possible to create stable cell lines of particularly desirable trophoblasts. See, for instance, Omi et al., Int J Mol Med. 23(2):229-36, (2009).

Accordingly, trophoblasts can be adhered to any of the materials described herein which are then configured into three-dimensional matrices. As described elsewhere herein a patch of matrix-forming material can be seeded with trophoblast cells by innoculating the patch with an amount of trophoblast cells and then incubating the seeded patch in carbon dioxide environment to allow cell attachment to the matrix. See Ma et al. (1999) for details on the cell adhesion parameters for ED27 trophoblast cells. Cells that are not washed away become attached to the fiber surface by adhesion or interception. See page 716 of Ma et al. (1999). Ma (1999) estimated that the seeding efficiency of this process was about 30% for a variety of fibrous matrixes tested. See Table 2 at page 717 of Ma et al. (1999).

8. Types of Matrices

Ma et al., Biotechnol. Prog. 15, pp. 715-724 (1999), which is incorporated herein by reference, described various fibrous and nonwoven materials for tissue-engineering purposes. Ma explains that fibrous material is popular for such purposes because of its high specific surface area, excellent mechanical properties, high void volume, and three-dimensional structure, all of which together are desirable parameters for high-density cell and tissue cultures.

The three dimensional scaffold of the present technology can be formed from any material. Such a material may be biocompatible, i.e., it is able to exist and perform in a living tissue or a living system by not being toxic or injurious and not causing immunological rejection. Such a material may also be biodegradable and capable of being broken down into innocuous products when placed within a living system, such as a cell culture system, or a living organism, such as a human or animal, or when exposed to body fluids. A matrix may also be bioerodible, that is, capable of being dissolved or suspended in biological fluids) and/or bioresorbable, i.e., capable of being absorbed by the cells, tissue, or fluid in a living body. See US 20090239298.

The matrix can be made from nonwoven fabrics such as polyglycolic acid (PGA) and polylactice acid (PLA), which have been widely used for growing chondrocytes, smooth muscle cells, epithelial cells, keratinocytes, fibroblasts, nerve cells, and cardiac muscle. See Ma et al. (1999). Nonwoven fabrics are made by entangling fibers or filaments to form three-dimensional structures. Knitted fabrics also provide well-defined textures in two or three dimensions, but Ma et al. (1999) recommends nonwoven fabrics as ideal for forming three-dimensional structures.

Various parameters of fibrous materials can be modified to help improve growth of such cells in vitro. For instance, spatial patterning of biochemical ligands, cell seeding method and density, scaffold thickness, surface texture, fiber diameter, orientation, porosity, and woven and knitting characteristics all contribute to the environment in which embryonic stem cells of the present technology may be cultured into embryoid bodies. Thus, the size of the fibrous pores, cell seeding and density, and fiber thickness can be varied and optimized to provide alternative conditions within which to seed trophoblasts and for shaping into three-dimensional compartments for ES cell seeding. The surface texture also is important for controlling cell adhesion, shape, proliferation, and function of the trophoblast cells.

One useful fabric is polyethylene teraphthalate (PET). PET fabrics have previously been used as support matrixes to grow human trophoblast cells (Ma, et al., Biotechnology and Bioengineering, Vol. 70, No. 6: 606-618, 2000). Other researchers have suggested that PAU-coated PTFE fabric could be a useful scaffolding biomaterial for developing bio-artificial organs (Soto, et al., E-Gnosis [online], Vol. 4, Art. 10: 1-10, 2006). PLLA, PGA, and PCL, when incorporated into stem cell cultures, mimic the stem cell niche and aid in stem cell growth and differentiation (Dawson et al., Advanced Drug Delivery Reviews, Vol. 60, Issue 2: 215-228, 2008). Other synthetic polymers useful for making matrix scaffolds include nonwoven polyglycolic acid (PGA) and polylactic acid (PLA), which have been used for tissue engineering of chondrocytes, smooth muscle cells, epithelial cells, keratinocytes, fibroblasts, nerve cells, and cardiac muscle. See Ma et al., (1999). Accordingly, examples of synthetic polymers which can be used in accordance with the present invention include but are not limited to poly(hydroxy acids) such as poly(lactic acid) (PLA), poly(L-lactic acid) (PLLA), poly (glycolic acid) (PGA), poly(lactic acid-co-glycolic acid) (PLGA), poly(L-lactic acid-co-glycolic acid) (PLLGA), polyanhydrides, polyorthoesters, poly(ester amides), polyamides, poly(ester ethers)polycarbonates, polyalkylenes such as polyethylene and polypropylene, polyalkylene glycols such as poly(ethylene glycol) (PEG), polyalkylene oxides such as poly(ethylene oxide) (PEO), polyalkylene terephthalates such as poly(ethylene terephthalate), polyvinyl alcohols (PVA), polyvinyl ethers, polyvinyl esters such as poly(vinyl acetate), polyvinyl halides such as poly(vinyl chloride) (PVC), polyvinylpyrrolidone, polysiloxanes, polystyrene (PS), polyurethanes, derivatized celluloses such as alkyl celluloses, hydroxyalkyl celluloses, cellulose ethers, cellulose esters, nitro celluloses, polymers of acrylic acids, such as poly(methyl(meth)acrylate) (PMMA), poly(ethyl(meth) acrylate), poly(butyl(meth)acrylate), poly(isobutyl(meth) acrylate), poly(hexyl(meth)acrylate), poly(isodecyl(meth) acrylate), poly(lauryl(meth)acrylate), poly(phenyl(meth) acrylate), poly(methyl acrylate), poly(isopropyl acrylate), poly(isobutyl acrylate), poly(octadecyl acrylate) and copolymers and mixtures thereof, polydioxanone and copolymers thereof, polyhydroxyalkanoates, poly(propylene fumarate), polyoxymethylene, and poloxamers. Further examples of biodegradable synthetic polymers include poly(hydroxy acids) such as PLA, PGA, PLGA, and copolymers with PEG; polyanhydrides, poly(ortho)esters, polyurethanes, poly(butyric acid), poly(valeric acid), poly(lactide-co-caprolactone), trimethylene carbonate, and other polymers which are described in U.S. Pat. Nos. 5,654,381; 5,627,233; 5,628,863; 5,567,440; and 5,567,435. Typically, these polymers degrade in vivo by both non-enzymatic and enzymatic hydrolysis, and by surface or bulk erosion.

In another embodiment, the three-dimensional matrix of the present technology comprises a natural biomaterial, selected from the group consisting of collagen, fibrinogen, fibrin, hyaluronic acid, alginate, coralline, glycosaminoglycans (GAGs), hydroxyapatite (HA), cellulose, chitosan, silk fibroin and Matrigel. These natural biomaterials, when incorporated into stem cell cultures effectively mimic the stem cell niche and thereby aid in stem cell growth and differentiation. See Dawson et al., Advanced Drug Delivery Reviews, Vol. 60, Issue 2: 215-228, 2008). Further examples of natural polymers which can be used in accordance with the present technology include but are not limited to polypeptides and polysaccharides such as alginate, dextran, and celluloses; collagens, including derivatized collagens, e.g., alkylated, hydroxylated, oxidized, or PEG-lated collagens, as well as collagens modified by other alterations routinely made by those skilled in the art; hydrophilic proteins such as albumin; hydrophobic proteins such as protamines, and copolymers and mixtures thereof. Typically, these polymers degrade by enzymatic hydrolysis, by exposure to water in vivo, or by surface or bulk erosion.

Fabrics can be compressed to form three-dimensional structures such as by thermal compression at 121° C. by a weight for a period of time to reduce the thickness of the fibrous material to about 1 mm. Such heating and weighting processes can help create fabrics of different densities and porosities. See Table 1 of Ma et al. (1999) for comparisons of the physical parameters of nonwoven and knitted PET fabrics with and without thermal compression.

9. Seeding Trophoblasts Onto Matrix Materials

A patch of PET can be seeded with trophoblast cells by innoculating the patch with a known amount of trophoblast cells and then incubating the seeded patch in carbon dioxide environment to allow cell attachment to the matrix. See Ma et al. (1999) for details on the cell adhesion parameters for ED27 trophoblast cells. Basically, a fabric patch is autoclaved, incubated in a CO2 incubator overnight and then innoculated with trophoblast cells for about an hour to all for cell attachment to the fibrous matrix. After washing, the cells retained inside the matrix are cells attached to the fiber surface by adhesion or interception. See page 716 of Ma et al. (1999). Ma (1999) estimated that the seeding efficiency of this process was about 30% for a variety of fibrous matrixes tested. See Table 2 at page 717 of Ma et al. (1999).

10. Configuration and Porosity Parameters of Matrix Materials/Fabrics

The matrix can then be shaped into a three-dimensional configuration. Methods of generating porous scaffolds are described in US 20090239298, see for instance the Materials and Experimental Procedures section of the Examples, and U.S. Pat. Nos. 6,471,993 and 6,365,149 and references therein, which are all incorporated by reference. See also Hutmacher (2001), Journal of Biomaterials Science—Polymer Edition 12(1) 107-124, which concerns scaffold design and fabrication technologies for engineering tissues. The pore size and density of the porous scaffold can be controlled by polymer chemistry and the synthesis methods. A porous scaffold of the present technology has a pore size in a range between 10-1,000 µm, between 100-1,000 µm, between 400-800 µm, between 400-700 µm, between 400-600 µm, or between 400-500 µm. A porous scaffold may have an average distance between the pores in a range between 5-500 µm, between 5-400 µm, between 5-300 µm, between 5-200 µm, or between 5-100 µm. Furthermore, a scaffold of the present technology may have an average porosity of at least 70%, preferably at least 80%, more preferably at least 90%, say 95%. Scaffold porosity may be measured as described in U.S. Pat. No. 6,471,993. The term "scaffold" as used herein is synonymous with matrix or fabric as used herein to describe the structure that is made to comprise trophoblast cells for providing an in vivo-like environment for producing EBs from hESCs for making organ-specific stem cells.

The present technology is not limited to the use of only a 96-well plate; any vessel or compartment can be used as a housing within which a three-dimensional matrix can be placed. For instance, a matrix may be placed into an eppendorf tube or test tube or plastic or glass centrifuge tube, or into a larger chamber such as those used for large-scale cell culture, such as a bioreactor chamber. Alternatively, if a matrix is embedded into a hydrogel, that hydrogel unit may be placed on any convenient or suitable surface, such as on an agar plate, or petri dish, which permits stability of the hydrogel and subsequent growth of the embryoid body in the matrix located within the hydrogel.

Into the trophoblast-containing matrix are seeded ES cells as disclosed above. Accordingly, the ES cells will develop not only in the presence of culture medium present in, for example, a hydrogel in the well, but also nurtured by the in vivo-like presence of the trophoblasts and the nutrients they naturally produce. See Ma et al. (1999). The culture medium used to induce ESC differentiation can be knockout KO-DMEM medium which is a water-based medium that includes salts and essential proteins (Gibco-Invitrogen Corporation products, Grand Island, N.Y., USA). The culture medium may include serum or serum replacement. Serum may be provided at a concentration of at least 5%, at least 15% or at least 20%. To reduce intracellular oxidative reactions, β-mercaptoethanol, an anti-oxidant agent, can be added to the culture medium, as well as antibiotics such as penicillin and streptomycin to avoid bacterial contamination during culturing. Accordingly, in one embodiment, culture medium of the present technology may include 80% KO-DMEM, 20% serum, 0.5% Penicillin-Streptomycin, 1 mM L-glutamine, 0.1 mM β-mercaptoethanol and 1% non-essential amino acid stock (Gibco-Invitrogen Co.).

The present technology therefore encompasses a matrix-suitable material, such as a fibrous material described above, that comprises trophoblast cells, which is configured into a three-dimensional shape into which ES cells are seeded. Alternatively, a matrix material may be already formed into a pre-configured structure, such as already formed into a three-dimensional shape, which is then submerged in a solution comprising trophoblast cells such that the pre-formed structure contains trophoblasts, such as trophoblasts that are adhered to fibers or filaments or other structures within the fabric. One desirable structure of the matrix is in the form of a pocket or well into which embryonic stem cells can be seeded surrounded by the pre-treated trophoblast environment within the three-dimensional matrix. The trophoblast cells within the matrix provide nutrients and hormones to the ES cells to promote formation of EBs. An example of trophoblast cells are the ED27 cells obtained from human first-trimester chorionic villi. These cells are prepared for culturing in phenol-red free Ham's F12/Dulbecco's modified Eagle's medium, supplemented with 15% fetal bovine serum, 2 mM L-glutamine, 1 mM sodium pyruvate, and 50 μg/mL gentamicin sulfate. See Ma et al., Biotechnol. Bioeng., 70, pp. 606-618 (2000), which is incorporated herein by reference.

Ma et al. (2000) studied long-term cultures of trophoblast cells grown in three-dimensional and two-dimensional PET matrices. In those long-term culture experiments, the fabric matrix innoculated as described above was transferred to a new well after 72 hours and media was replaced with fresh media every three days over 21 days. Ma (2000) concluded that low porosity PET fabric matrices give a higher cell proliferation rate due to its increased surface ability. See page 610. Low porosity matrices had 85% porosity with a pore size of 8 to 25 μm in radius, with an average pore radius of ~15 μm. As culturing time continued, more estradiol was produced in both low and high porosity fabrics but the estradiol production level was more prominent for cells grown in the high porosity PET matrix. The high porosity fabric had 90% porosity with an average pore radius of ~20 μm. Thus, Ma (2000) demonstrated that the increase in estradiol production in the high porosity PET fabric was attributable to cells undergoing physiological change or biochemical differentiation. The difference in pore size may contribute to differences in cell morphology and spatial organization in the three-dimensional matrix leading to differences in production of estradiol and other hormones. Accordingly, the differences between the low and high porosity fabric studies indicate that pore size is important in determining cell morphology, proliferation, differentiation, and tissue function.

11. Chemicals and Growth Factors

In addition, agents and chemicals can be added to media disclosed herein to induce differentiation of particular lineages from ES cells and embryoid bodies. For instance, transforming growth factor-β is useful for inducing cartilage formation, insulin-like growth factor is useful for inducing the formation of large open tubular structures and liver cells; retinoic acid is useful in inducing formation of small circular multilayered bodies, and activin-A is useful for inducing liver cells and tissues. See Levenberg et al. PNAS, Vol. 100, No. 22:12741-12746 (2003). Thus, in one embodiment, a three dimensional matrix is exposed to a serum-free environment comprising an agent, selected from the group consisting of growth factors stem cell factor (SCF), thrombopoietin (TPO), Flt-3 ligand (Flt-3L), bone morphogenic protein-4 (BMP-4), vascular endothelial growth factor (VEGF) and combinations thereof. Such growth factors have been shown to aid embryoid body-mediated hematopoiesis from human embryonic stem cells. See Tian et al., Experimental Hematology, Vol. 32, Issue 10: 1000-1009, 2004.

12. Differentiating ES Cells

It is possible to induce ES cells to differentiate into particular lineages, such as but not limited to into cartilage, liver tissue, neural tissue, and blood vessels, by monolayer culturing or suspension growth. See Levenberg et al., PNAS, Vol. 100, No. 22:12741-12746 (2003), Levenberg et al., PNAS, Vol. 99, No. 7:4391-4396 (2002), and US 2009/0203129 (2009), which are incorporated herein by reference. By exposing ES cells to various permutations of growth factors, chemokines, and cytokines, for example, the skilled person can induce ES cells to form embryoid bodies, which can subsequently be induced to differentiate into a desired organ-specific stem cell. For instance, US 20090239298, describes how EBs can be forced to differentiate into neural precursors in medium comprising DMEM/F-12 medium with 5 mg/ml insulin, 50 mg/ml transferrin, 30 nM selenium chloride, and 5 mg/ml fibronectin. The resultant neural precursors can be further transplanted to generate neural cells in vivo.

EBs can differentiate to oligodendrocytes and myelinate cells by culturing the cells in modified SATO medium, i.e., DMEM with bovine serum albumin (BSA), pyruvate, progesterone, putrescine, thyroxine, triiodothryonine, insulin, transferrin, sodium selenite, amino acids, neurotrophin 3, ciliary neurotrophic factor and Hepes.

EBs also can differentiate into mast cells by culturing them in DMEM medium supplemented with 10% FCS, 2 mM L-glutamine, 100 units/ml penicillin, 100 mg/ml streptomycin, 20% (v/v) WEHI-3 cell-conditioned medium and 50 ng/ml recombinant rat stem cell factor.

To generate hemato-lymphoid cells, EBs can be transferred to gas-permeable culture dishes in the presence of 7.5% $CO_2$ and 5% $O_2$ using an incubator with adjustable oxygen content. See US 20090239298, which is incorporated herein by reference.

Other typical growth factors that help induce differentiation of EBs into specific lineages include, but are not limited to, basic fibroblast growth factor, transforming growth factor β, activin-A, bone morphogenic protein 4, hepatocyte growth factor, epidermal growth factor, nerve growth factor, and retinoic acid. These are illustrative examples of culturing conditions and it is within the purview of the skilled artisan to select and formulate media suitable for the differentiation and expansion of the isolated lineage specific cells, which includes various tissue culture medium, growth factors, antibiotic, amino acids etc.

In addition, a hydrogel in which the three-dimensional matrix may be embedded may also comprise one or more agents selected from the group consisting of retinoic acid, transforming growth factor β, activin-A, insulin-like growth factor, acidic fibroblast growth factor, bFGF, bone morphogenic protein-4 (BMP-4), vascular endothelial growth factor (VEGF), SCF, erythropoietin, thyroid hormone, and eotaxin, and combinations thereof. As mentioned, growth factors, retinoic acid, transforming growth factor β, activin-A, and insulin-like growth factor induce the differentiation on three-dimensional polymer scaffolds of human embryonic stem cells into three-dimensional structures with characteristics of neural tissue, cartilage, and liver, respectively. See Levenberg et al., PNAS, Vol. 100, No. 22: 12741-12746, 2003. When added to stem cell culture media or a hydrogel, for instance, acidic fibroblast growth factor and bFGF induce hepatic maturation of embryoid bodies derived from mouse embryonic stem cells (Chinzei, et al., Hepatology, Vol. 36, No. 1: 22-29, 2002). Embryoid body differentiation in BMP4 directs the expression of erythroid-specific transcription factors and the expression of such transcription factors can be further stimulated by the inclusion of VEGF, SCF, erythropoietin, and thyroid hormone. See Adelman et al., Development, 129: 539-549, 2002. Eotaxin acts synergistically with SCF to accelerate myelopoiesis and the differentiation of embryonic mast cell progenitors. See Quackenbush, et al., Blood, Vol. 92, No. 6: 1887-1897, 1998.

13. Migration of Organ-Specific Cells from EBs

These organ-specific cells, which have differentiated from the embryoid bodies grown from the seeded ES cells within the trophoblast-containing matrix, can migrate from the matrix compartment and into the well and/or hydrogel that is holding the matrix. One can select the chemokines and morphogens such that particular organ-specific cells will migrate out of the EB and into the holding well and thus be isolated. For instance, if SDF-1 (stromal cell-derived factor-1) is used as a chemoattractant, then organ-specific cells that express CXCR4 and thus are committed to neuronal and hematopoietic lineages, will differentiate from cells of the EB. SDF-1 chemokine, chemokine monocyte chemoattractant protein-1, and cytokine stem-cell factor have been found to attract neural stem cells to the sites of brain injuries and tumors. See Jurvansuu et al., Cancer Res, 68(12), pp.: 4614-4622 (2008). The EGFL7 protein acts as a chemoattractant for embryonic endothelial cells and fibroblasts and functions in the maintenance of endothelial integrity. See Campagnolo et al., American Journal of Pathology, 167: 275-284, 2005. Similarly, PDK1 is essential for the migration, in response to vascular endothelial growth factor-A, of vascular endothelial cells differentiated from mouse embryonic stem cells. See Primo et al., JCB, Vol. 176 No. 7: 1035-1047, 2007. FGFs perform a signaling role during early vertebrate development and orchestrate gastrulation movements by acting as chemoattractants. See Böttcher, R. T., and C. Niehrs, Endocrine Reviews, 26(1): 63-77, 2005. In this regard, therefore, it is well known that such chemoattractants, chemokines, and chemokine receptors help promote chemotaxis. Chemokines and chemokine receptors, such as SDF-1 and CXCR4, for example, have also been implicated in the blastocyst differentiation (McGrath et al., Developmental Biology, 213, 442-456, 1999). SDF-1 is localized in extracellular matrix and any disruption in the SDF-1 and CXCR4 chemotaxis may result in misguided migration of stem cells; for example, hematopoietic stem cells and progenitor cells will migrate from marrow into blood circulation (Ma et al., Immunity. 10(4): 463-71, 1997) and the programmed development of cerebellum neurons will be derailed (Ma et al., PNAS, 95(16), 9448-9453, 1998). Thus, by using such seeding strategies, differentiation agents, and chemoattractants, organ- or lineage-specific cells can be readily obtained, isolated, and then cultured independently.

Methods of isolating EB-derived-differentiated cells via FACS analysis are known in the art. See US 20090239298. For instance, in one method, EBs are disaggregated using a solution of Trypsin and EDTA (0.025% and 0.01%, respectively), washed with 5% fetal bovine serum (FBS) in phosphate buffered saline (PBS) and incubated for 30 min on ice with fluorescently-labeled antibodies directed against cell surface antigens characteristics to a specific cell lineage. For example, US 20090239298 describes that endothelial cells are isolated by attaching an antibody directed against the platelet endothelial cell adhesion molecule-1 (PECAM1) such as the fluorescently-labeled PECAM1 antibodies (30884.times.) available from PharMingen (PharMingen, Becton Dickinson Bio Sciences, San Jose, Calif., USA) as described in Levenberg, S. et al., Endothelial cells derived from human embryonic stem cells. Proc. Natl. Acad. Sci. USA. 2002. 99: 4391-4396. Hematopoietic cells are isolated using fluorescently-labeled antibodies such as CD34-FITC, CD45-PE, CD31-PE, CD38-PE, CD90-FITC, CD117-PE, CD15-FITC, class I-FITC, all of which IgG1 are available from PharMingen, CD133/1-PE (IgG1) (available from Miltenyi Biotec, Auburn, Calif.), and glycophorin A-PE (IgG1), available from Immunotech (Miami, Fla.).

14. General Summary

Accordingly, the present technology provides a method for creating and isolating organ-specific stem cells by seeding embryonic stem cells into a trophoblast-containing, three-dimensional matrix, growing an embryoid body from the embryonic stem cells within the trophoblast-containing matrix; and transferring the matrix containing the embryoid body to a new environment that contains at least one agent that promotes the creation of organ-specific stem cells from the embryoid body. The organ-specific stem cells can then be readily isolated.

As described above, it is known how to obtain trophoblast cells and use them to impregnate a matrix-suitable fabric with trophoblasts, which in turn can be shaped into a three-dimensional compartmental matrix within which ES cells can be seeded. Also described herein are the chemicals and agents useful for promoting formation of embryoid bodies from ES cells, as well as the agents that promote the differentiation of the embryoid body into particular organ-specific cell types.

Thus, it is possible, in one 96-well plate to fill the same medium, e.g., nutrient-infused hydrogels, in each or several wells, place a trophoblast-containing matrix in each medium-containing well, and seed each matrix with the same number of ES cells. Consequently, each clump of ES cells will develop into an embryoid body, and each embryoid body in turn will differentiate into, and produce, the desired organ-specific cells. Those organ-specific cells can then be isolated from each well. Accordingly, one 96-well plate can produce many lots of the same organ-specific cells, which can then be pooled and independently cultured.

Alternatively, different media can be placed in different wells of a single 96-well plate such that different organ-specific cell types are produced from the formed embryoid bodies. Similarly, different numbers of ES cells can be seeded into different trophoblast-containing matrices such that EBs of different sizes can be formed, which will induce the formation of different cell types.

Moreover, multiple 96-well plates containing the same or different media can be employed simultaneously to bulk up or scale up the production of particular types of organ-specific cells per unit time. The present technology thus can be adapted for use in a bioreactor, which can be automated to move matrices from one well to another that contains desired nutrients and growth factors to create a robust and productive method and apparatus for producing bulk quantities of organ-specific cells. Furthermore, a 96-well plate setting with the EB-Trophoblast-matrix insider can be used for high throughput screening of compounds and biologics that may affect the differentiation and migration of organ-specific stem cells or progenitor cells.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 particles refers to groups having 1, 2, or 3 particles. Similarly, a group having 1-5 particles refers to groups having 1, 2, 3, 4, or 5 particles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference in their entireties and for all purposes to the same extent as if each individual publication, patent, or patent application was specifically and individually incorporated by reference in its entirety for all purposes.

Example 1

An Illustrative Embodiment of a Procedure

Step 1: Seeding Embryonic Stem Cells into a 3D Trophoblast Matrix

Using a micropipe, a clump of ES cells is picked from an individual colony of ES cells and placed into a hydrogel microbead, such as agarose. The encapsulated ES cells are then seeded carefully into the center of a trophoblast-containing matrix positioned in a well of a 96-well plate.

Step 2: Growing the Embryoid Body

The clump of ES cells aggregates and forms an embryoid body that has complex internal structures, such as a yolk sac and cardiomyocytes. Once heart muscle cells begin to beat rhythmically, then the EB can be further manipulated.

Step 3: Loosening the Embryoid Body

The EB that is embedded within the trophoblast-containing matrix can be moved through a series of solutions in corresponding wells of the same (or different) 96-well plate to dissolve away the hydrogel, and to digest newly-formed extracellular matrix material, such as by using trypsin/EDTA.

Step 4: Isolating Organ-Specific Cells

The trophoblast-containing matrix containing the loosened EB is transferred to a new well of a fresh 96-well plate pre-filled with a hydrogel or coated with a chemokine or morphogen, or both. After a period of time, the differentiated organ-specific cells are attracted to these agents and migrate out of the embryoid body and the matrix and can be isolated from the bottom of the well or the surrounding hydrogel.

Example 2

Making a Trophoblast-Containing Matrix

PET fabric can be treated with 1% NaOH solution at boiling temperature for 1 hour to reduce surface hydrophobicity and to increase biocompatibility. The fabric can then be cut into patches. Total fiber volume can be determined by weight of the patch divided by the PET fabric density. The thickness and diameter of the patch can also be used to determine the volume of the fabric matrix and its porosity.

The patch then can be placed into a 6-well plate, autoclaved, and incubated with culture medium in a $CO_2$ incubator overnight. Seeding cultures of trophoblast cells can be prepared by trypsinizing them to make a cell suspension. A known amount of those suspended cells, e.g., $8\text{-}10\times10^6$, can then be added to the patch in the well and incubated in a $CO_2$ incubator for about 1 hour to allow for the cells to attach to the fabric patch. The trophoblast-seeded patch can then be transferred to a new well and washed with media to remove unattached cells, and then placed into a new well. See the Materials and Methods section of Ma et al., Biotechnol. Prog., 15: 715-724 (1999).

The trophoblast-seeded patch can then be shaped into a three-dimensional compartmental matrix structure. See the discussion elsewhere herein on methods for forming and structuring a three-dimensional matrix.

Example 3

EB Growth and Production of Organ-Specific Cells

A clump of human ES cells can be carefully placed into a hydrogel microbead and transferred into a trophoblast-containing matrix compartment that is positioned within well of a 96-well plate. Human EBs can be grown in medium that lacks lymphocyte inhibitory factor (LIF) to promote differentiation. The medium can then be supplemented with a growth factor, such as basic fibroblast growth factor, transforming growth factor β, activin-A, bone morphogenic protein 4, hepatocyte growth factor, epidermal growth factor, nerve growth factor, and retinoic acid.

After a period of time, the matrix can be transferred to a fresh well containing a chemokine or morphogen that encourages the migration of the resultant organ-specific cells produced by the EB in the presence of the particular growth factor, out of the EB and matrix and into the well. The organ-specific cells can then be isolated and used as desired.

What is claimed is:

1. A method for creating lineage-specific stem cells, comprising:
    a) seeding human embryonic stem cells (hESCs) into a trophoblast-containing three-dimensional matrix;
    b) growing an embryoid body from the human embryonic stem cells within the trophoblast-containing matrix;
    c) transferring the trophoblast-matrix containing the embryoid body from step (b) into a new culture medium that contains at least one differentiation agent that causes the ES cells to become committed lineage-specific stem cells; and
    d) transferring the trophoblast-matrix containing the embryoid body from step (c) into a new culture medium that contains at least one chemoattractant, wherein at least one committed lineage-specific stem cell migrates out of the embryoid body and the trophoblast-containing matrix in response to the chemoattractant.

2. The method of claim 1, further comprising encapsulating human embryonic stem cells in a hydrogel.

3. The method of claim 1, further comprising degenerating the structure of the embryoid body.

4. The method of claim 3, wherein degenerating the structure of the embryoid body comprises digesting the trophoblast-containing matrix comprising the embryoid body.

5. The method of claim 4, further comprising isolating lineage-specific stem cells obtained from the degenerated embryoid body.

6. The method of claim 2, wherein the hydrogel comprises a natural or synthetic polymer.

7. The method of claim 6, wherein the hydrogel comprises a polysaccharide, a peptide, a proteoglycan, or a combination thereof.

8. The method of claim 2, wherein the hydrogel comprises a polymer selected from the group consisting of poly(glycolic acid), poly(lactic acid), poly(glycolic acid-co-lactic acid), collagen, laminin, hyaluronan, alginate, chitosan, silk fibrils, poly(vinyl alcohol), poly(2-hydroxylethyl methacrylate), polyethylene terephthalate, agarose, methylcellulose, fibrin, and a combination thereof.

9. The method of claim 2, wherein the trophoblast-containing matrix is embedded in a hydrogel that is in a well of a 96-well plate.

10. The method of claim 2, wherein the step of transferring the trophoblast-matrix containing the embryoid body to a new culture medium comprises:
  (i) dissolving the hydrogel and
  (ii) transferring the trophoblast-containing matrix containing the embryoid body into a 96-well plate that is either (a) pre-filled with a hydrogel that comprises at least one differentiation agent for promoting the creation of lineage-specific stem cells, or (b) coated with at least one differentiation agent for promoting the creation of lineage-specific stem cells.

11. The method of claim 10, wherein the differentiation agent is a chemokine or morphogen.

12. The method of claim 1, wherein the trophoblasts are cytotrophoblast cells.

13. The method of claim 1, wherein 10-100,000 human embryonic stem cells are seeded into the trophoblast-containing matrix.

14. The method of claim 1, wherein the differentiation agent promotes the creation of neural stem cells, oligodendrocyte cells, mast cells, hemato-lymphoid cells, epithelial cells, mammary stem cells, mesenchymal stem cells, olfactory stem cells, and testicular stem cells.

15. The method of claim 10, wherein multiple wells of the 96-well plate each contain a trophoblast-containing matrix seeded with embryonic stem cells, and each matrix, when it comprises a grown embryoid body, is simultaneously or subsequently transferred to a well plate that comprises at least one differentiation agent that promotes creation of the same or different lineage-specific stem cell.

16. The method of claim 1, wherein the trophoblast containing-matrix is transferred to a new culture medium once the embryoid body develops beating cardiomyocytes.

* * * * *

UNITED STATES PATENT AND TRADEMARK OFFICE
CERTIFICATE OF CORRECTION

PATENT NO. : 9,102,914 B2  
APPLICATION NO. : 13/257949  
DATED : August 11, 2015  
INVENTOR(S) : Gu Page 1 of 1

It is certified that error appears in the above-identified patent and that said Letters Patent is hereby corrected as shown below:

In the Specification

In Column 1, Line 9, delete "0371" and insert -- § 371 --, therefor.

In Column 11, Line 49, delete "CO2" and insert -- $CO_2$ --, therefor.

Signed and Sealed this
Twenty-eighth Day of June, 2016

Michelle K. Lee
*Director of the United States Patent and Trademark Office*